United States Patent [19]

Kok et al.

[11] Patent Number: 5,156,940
[45] Date of Patent: Oct. 20, 1992

[54] PHOTOGRAPHIC STABILIZERS WITH 1-PHENYL-3-PYRAZOLIDINONE MOIETIES

[75] Inventors: Piet Kok, Gent; Jos A. Vaes, Betekom; Jean-Marie O. Dewanckele, Drongen; Luc J. Wabbes, Mortsel, all of Belgium

[73] Assignee: AGFA-Gevaert, N.V., Mortsel, Belgium

[21] Appl. No.: 654,682

[22] Filed: Feb. 13, 1991

[30] Foreign Application Priority Data

Feb. 26, 1990 [EP] European Pat. Off. ........... 90200458

[51] Int. Cl.$^5$ .................. G03C 5/54; G03C 1/34; G03C 1/42
[52] U.S. Cl. .................. 430/230; 430/204; 430/234; 430/249; 430/440; 430/445; 430/483; 430/489; 430/566; 430/611; 430/614
[58] Field of Search ............ 430/218, 219, 230, 234, 430/249, 440, 445, 483, 489, 566, 611, 614, 204

[56] References Cited

U.S. PATENT DOCUMENTS 4,845,020  7/1989  Itoh et al. ................ 430/445

*Primary Examiner*—Richard L. Schilling
*Attorney, Agent, or Firm*—Breiner & Breiner

[57] ABSTRACT

A new class of photographic stabilizers is prepared and their use in photographic materials is disclosed. These compounds are 1-phenyl-3-pyrazolidinone derivatives corresponding to following general formula:

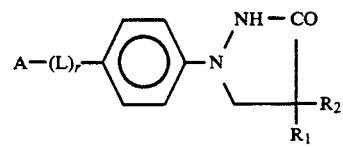

wherein:

A represents a group capable of adsorbing at the surface of silver halides;

L is a divalent linking group and r is 0 or 1;

R1 and R2 each represent hydrogen, lower alkyl or substituted lower alkyl.

The photographic materials containing the substances of the invention are preferably DTR mono-sheet elements which after processing can serve as planographic printing plates.

4 Claims, No Drawings

PHOTOGRAPHIC STABILIZERS WITH 1-PHENYL-3-PYRAZOLIDINONE MOIETIES

BACKGROUND OF THE INVENTION

The present invention relates to the preparation of a new class of photographic stabilizers and their use in photographic silver halide emulsions and materials.

As known to those skilled in the art an antifoggant or fog-inhibiting compound reduces the fog level of a developed freshly coated photographic emulsion by decreasing the rate of development of fog centers relative to the rate of development of latent image; on the other hand stabilizers inhibit fog increase during longer periods of storage of the coated photographic material. Since many classes of useful compounds to some degree exhibit both properties the term "stabilizer" in the following text will refer to compounds eventually exhibiting both functions.

Many known compounds can be added as fog-inhibiting agent or stabilizer to the silver halide emulsion. Suitable examples are i.a. the heterocyclic nitrogen-containing compounds such as benzothiazolium salts, nitroimidazoles, nitrobenzimidazoles, chlorobenzimidazoles, bromobenzimidazoles, mercaptothiazoles, mercaptobenzothiazoles, mercaptobenzimidazoles, mercaptothiadiazoles, aminotriazoles, benzotriazoles (preferably 5-methyl-benzotriazole), nitrobenzotriazoles, mercaptotetrazoles, in particular 1-phenyl-5-mercapto-tetrazole, mercaptopyrimidines, mercaptotriazines, benzothiazoline-2-thione, oxazoline-thione, triazaindenes, tetrazaindenes and pentazaindenes, especially those described by Birr in Z. Wiss. Phot. 47 (1952), pages 2–58, triazolopyrimidines such as those described in GB-A 1,203,757, GB-A 1,209,146, JA-Appl. 75-39537, and GB-A 1,500,278, and substituted 7-hydroxy-s-triazolo-[1,5-a]-pyrimidines as described in U.S. Pat. No. 4,727,017, and other compounds such as benzenethiosulphonic acid, benzenethiosulphinic acid, benzenethiosulphonic acid amide. Other compounds that can be used as fog-inhibiting compounds are metal salts such as e.g. mercury or cadmium salts. Surveys of these and other useful stabilizers are given in Research Disclosure No. 18431 (Aug. 1979) chapter II, and Research Disclosure 307105 (Nov. 1989) chapter VI. The stabilizer most widely used in photographic materials is 7-hydroxy-5-methyl-s-triazolo-[1,5-a]-pyrimidine to which will be referred hereafter as Reference Compound R-1.

The fog-inhibiting agents or stabilizers can be added to the silver halide emulsion prior to, during, or after the ripening thereof and mixtures of two or more of these compounds can be used. Instead of being present in the photographic material itself the stabilizer(s) can be added to one or more processing solutions preferably the development bath.

An effective stabilizing agent showing no unwanted side effects should meet several demands. First of all it should be stable in common alkaline processing conditions. It should be odourless, non-toxic and non-corrosive. It should be a a transparent colourless compound itself and form a colourless compound with silver ions.

From uttermost importance, an ideal stabilizer should reduce the fog level of a photographic material, freshly coated or stored, without adversely affecting the sensitivity and/or gradation. Several classes of known stabilizers reduce the practically obtained sensitivity and/or gradation by hampering the developability of latent image containing silver halide emulsion grains. In some cases a partial solution of this problem can be found in the use of a special class of stabilizers disclosed in Research Disclosure No. 29759 (Jan. 1989) which are in fact an ionic combination of a fog-inhibiting moiety and a development activating moiety. Still there is need for a constant search for new classes of photographic stabilizers showing no desensitizing side effect.

This problem of sensitivity and gradation loss is particularely cumbersome in a special class of photograhic materials known as Diffusion Transfer Reversal materials ("DTR materials"). The principles of this silver complex diffusion transfer reversal process have been described e.g. in U.S. Pat. No. 2,352,014 and in the book "Photographic Silver Halide Diffusion Processes" by André Rott and Edith Weyde—The Focal Press—London and New York, (1972).

In the DTR-process non-developed silver halide of an information-wise exposed photographic silver halide emulsion layer material is transformed with a so-called silver solvent into soluble silver complex compounds which are allowed to diffuse into an image-receiving element and are reduced therein with a developing agent, generally in the presence of physical development nuclei, to form a silver image having reversed image density values ("DTR-image") with respect to the black chemically developed silver image obtained in the exposed areas of the photographic material.

A DTR-image bearing material can be used as a planographic printing plate wherein the DTR-silver image areas form the water-repellant ink-receptive areas on a water-receptive ink-repellant background. For example, typical lithographic printing plates are disclosed e.g. in Japanese Examined Patent Publication (Kokoku) 30562/73, Japanese Unexamined Patent Publications (Kokai) Nos. 21602/78, 103104/79, 9750/81 etc.

The DTR-image can be formed in the image-receiving layer of a sheet or web material which is a separate element with respect to the photographic silver halide emulsion material (a so-called two-sheet DTR element) or in the image-receiving layer of a so-called single-support-element, also called mono-sheet element, which contains at least one photographic silver halide emulsion layer integral with an image-receiving layer in waterpermeable relationship therewith. It is the latter mono-sheet version which is preferred for the preparation of offset printing plates by the DTR method.

Mono-sheet DTR materials intended to be used as planographic printing plates are spectrally sensitized to match the emission wavelength of low output lasers which are the illuminating units of modern type- and image-setting devices. Red sensitization for exposure by a HeNe laser or near infra-red sensitization for exposure by a semiconductor laser are preferred. However when such spectrally sensitized mono-sheet DTR materials are stabilized with classically used compounds such as Reference Compound R-1 the chemical developability of the exposed silver halide is so strongly hampered that the differentiation between the DTR silver and the black silver background is almost completely lost. In this way no DTR image with a usable sensitivity and gradation can be obtained and the material cannot be transformed by processing into a lithographic printing plate. A partial solution to this problem consists in using a class of stabilizers characterized by the presence of a hydrophilic solubilizing moiety in their chemical formula, e.g. p-carboxyphenyl-mercapto-tetrazole, and 7-sulfo-naphto-(2,3,-d)-oxazoline-2-thion-sodium salt which latter compound will be referred to furtheron as Reference Compound R-2. However when using this kind of stabilizers the recovery of the lost sensitivity in DTR materials is only partial. So it is clear that there is still a need for the development of new classes of stabilizers which show little or no unwanted side effects, especially no reduction of sensitivity and gradation.

It is a purpose of the present invention to provide such a new class of photographic stabilizers.

SUMMARY OF THE INVENTION

It is the purpose of the present invention to disclose the preparation of a new class of photographic stabilizers.

It is a further purpose of the present invention to provide a class of stabilizers that exhibit excellent antifogging properties and stabilization of sensitometric properties during long storage periods.

It is still a further purpose of the present invention to provide a class of stabilizers that cause no reduction of sensitivity or gradation, especially in mono-sheet DTR materials.

This new class of photographic stabilizers according to the present invention can be represented by the following general formula:

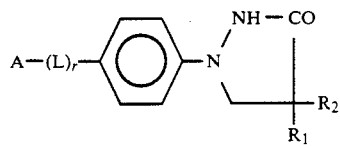

wherein:
A represents a group capable of adsorbing at the surface of silver halides;
L is a divalent linking group and r is 0 or 1;
$R_1$ and $R_2$ each represent hydrogen, lower alkyl or-substituted lower alkyl.

It is the presence of two photographically active functional groups in one molecule that gives this new class of stabilizers their special favourable properties especially its absence of desensitizing effects.

DETAILED DESCRIPTION

According to the present invention a photographic material composed of a support and at least one light-sensitive silver halide emulsion layer contains in the said emulsion layer or in a hydrophylic layer in water-permeable relationship therewith at least one 1-phenyl-3-pyrazolidinone derivative corresponding to the general formula:

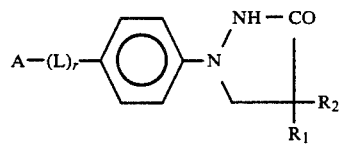

wherein:
A represents a group capable of adsorbing at the surface of silver halides;
L is a divalent linking group and r is 0 or 1;
$R_1$ and $R_2$ each represent hydrogen, lower alkyl or substituted lower alkyl.

The group A capable of being adsorbed to silver halide is preferably chosen from stabilizing groups present in the molecular structure of known stabilizing agents e.g. thiourea, triazoles, mercaptotetrazoles, mercaptoimidazoles, -thiazoles, -oxazoles, -triazoles, indazoles, imidazoles, benzimidazoles, 7-hydroxy-s-triazolo-[1,5-a]-pyrimidines etc.

$R_1$ and $R_2$ preferably each represent hydrogen, methyl or hydroxymethyl.

Examples for the divalent linking group L include alkylene, arylene, —CO—, —CO—NH—, —SO$_2$—NH— etc.

Examples of compounds according to the present invention are represented by the following general formula:

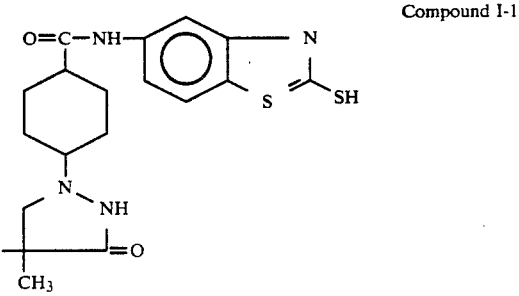

Compound I-1

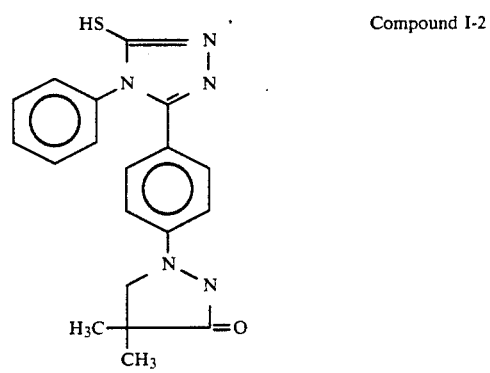

Compound I-2

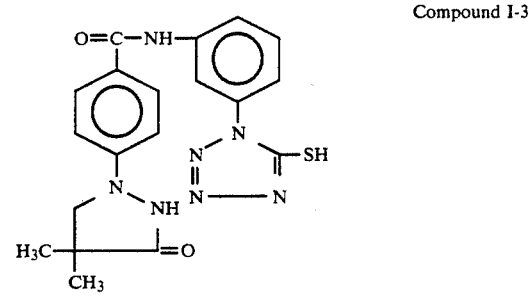

Compound I-3

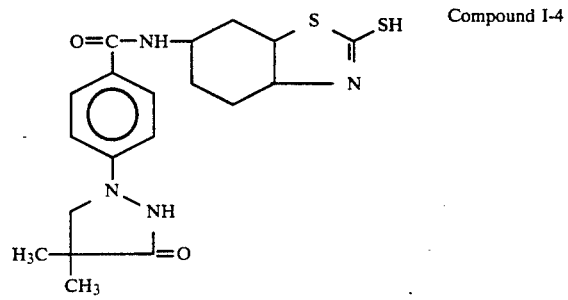

Compound I-4

-continued

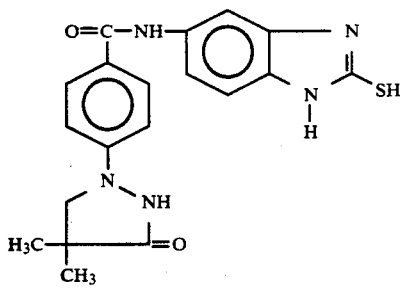
Compound I-5

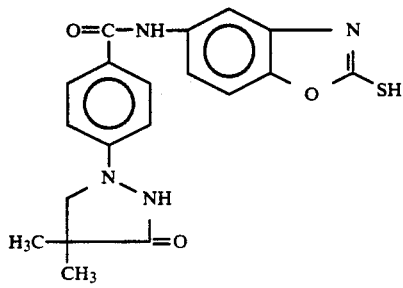
Compound I-6

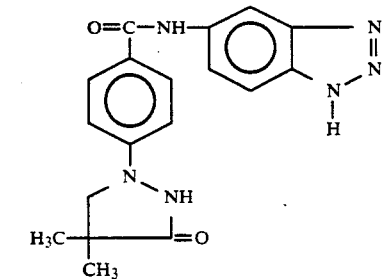
Compound I-7

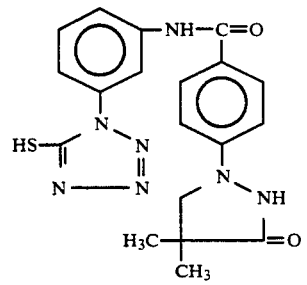
Compound I-8

The reference stabilizing agents R-1 and R-2 mentioned above are represented by the following chemical formula:

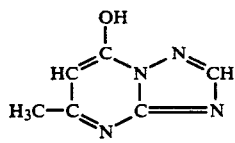
Compound R-1

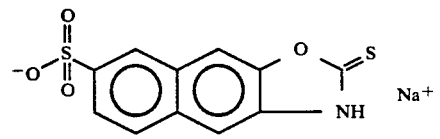
Compound R-2

The 1-phenyl-3-pyrazolidinone-derivatives ("Phenidone"-derivatives) according to the present invention can be added to a processing solution, e.g. a development bath, but preferably they are added to the photographic material itself. They can be added to any of the hydrophilic colloid layers of the photographic material, e.g. a non light sensitive intermediate layer, but preferably they are contained in the light sensitive emulsion layer(s) where they are most easily absorbed to the silver halide grain surface in order to exercise their function.

The halide composition of the silver halide emulsions used according to the present invention is not specifically limited and may be any composition selected from i.a. silver chloride, silver bromide, silver iodide, silver chlorobromide, silver bromoiodide, and silver chlorobromoiodide. The content of silver iodide is equal to or less than 20 mol %, preferably equal to or less than 5 mol %.

The photographic emulsions can be prepared from soluble silver salts and soluble halides according to different methods as described e.g. by P. Glafkides in "Chimie et Physique Photographique", Paul Montel, Paris (1967), by G. F. Duffin in "Photographic Emulsion Chemistry", The Focal Press, London (1966), and by V. L. Zelikman et al in "Making and Coating Photographic Emulsion", The Focal Press, London (1966). They can be prepared by mixing the halide and silver solutions in partially or fully controlled conditions of temperature, concentrations, sequence of addition, and rates of addition. The silver halide can be precipitated according to the single-jet method, the double-jet method, or the conversion method.

The emulsion can be desalted in the usual ways e.g. by dialysis, by flocculation and re-dispersing, or by ultrafiltration.

The silver halide particles of the photographic emulsions used according to the present invention may have a regular crystalline form such as a cubic or octahedral form or they may have a transition form. They may also have an irregular crystalline form such as a spherical form or a tabular form, or may otherwise have a composite crystal form comprising a mixture of said regular and irregular crystalline forms.

The silver halide grains may have a multilayered grain structure. According to a simple embodiment the grains may comprise a core and a shell, which may have different halide compositions, e.g. a bromide core and a chloride shell, and/or may have undergone different modifications such as the addition of dopes. Besides having a differently composed core and shell the silver halide grains may also comprise different phases inbetween.

Two or more types of silver halide emulsions that have been prepared differently can be mixed for forming a photographic emulsion for use in accordance with the present invention.

The average size of the silver halide grains may range between wide limits e.g. from 0.1 to 1.0 micron.

The size distribution of the silver halide particles of the photographic emulsions to be used according to the present invention can be homodisperse or heterodisperse. A homodisperse size distribution is obtained when 95% of the grains have a size that does not deviate more than 30% from the average grain size.

The silver halide crystals can be doped with $Rh^{3+}$, $Ir^{4+}$, $Cd^{2+}$, $Zn^{2+}$, $Pb^{2+}$ and $Pt^{2+}$.

Besides the silver halide another essential component of a light-sensitive emulsion layer is the binder. The binder is a hydrophilic colloid, preferably gelatin. Gelatin can, however, be replaced in part or integrallly by synthetic, semi-synthetic, or natural polymers. Synthetic substitutes for gelatin are e.g. polyvinyl alcohol, poly-N-vinyl pyrrolidone, polyvinyl imidazole, polyvinyl pyrazole, polyacrylamide, polyacrylic acid, and derivatives thereof, in particular copolymers thereof. Natural substitutes for gelatin are e.g. other proteins such as zein, albumin and casein, cellulose, saccharides, starch, and alginates. In general, the semi-synthetic substitutes for gelatin are modified natural products e.g. gelatin derivatives obtained by conversion of gelatin with alkylating or acylating agents or by grafting of polymerizable monomers on gelatin, and cellulose derivatives such as hydroxyalkyl cellulose, carboxymethyl cellulose, phthaloyl cellulose, and cellulose sulphates.

The binder should dispose of an acceptably high number of functional groups, which by reaction with an appropriate hardening agent can provide a sufficiently resistant layer. Such functional groups are especially the amino groups, but also carboxylic groups, hydroxy groups, and active methylene groups.

The gelatin can be lime-treated or acid-treated gelatin. The preparation of such gelatin types has been described in e.g. "The Science and Technology of Gelatin", edited by A. G. Ward and A. Courts, Academic Press 1977, page 295 and next pages. The gelatin can also be an enzyme-treated gelatin as described in Bull. Soc. Sci. Phot. Japan, No. 16, page 30 (1966).

The light-sensitive silver halide emulsion can be a so-called primitive emulsion, in other words an emulsion that has not been chemically sensitized. However, the light-sensitive silver halide emulsion can be chemically sensitized as described i.a. in the above-mentioned "Chimie et Physique Photographique" by P. Glafkides, in the above-mentioned "Photographic Emulsion Chemistry" by G. F. Duffin, in the above-mentioned "Making and Coating Photographic Emulsion" by V. L. Zelikman et al, and in "Die Grundlagen der Photographischen Prozesse mit Silberhalogeniden" edited by H. Frieser and published by Akademische Verlagsgesellschaft (1968). As described in said literature chemical sensitization can be carried out by effecting the ripening in the presence of small amounts of compounds containing sulphur e.g. thiosulphate, thiocyanate, thioureas, sulphites, mercapto compounds, and rhodamines. The emulsions can be sensitized also by means of gold-sulphur ripeners or by means of reductors e.g. tin compounds as described in GB-A 789,823, amines, hydrazine derivatives, formamidine-sulphinic acids, and silane compounds. Chemical sensitization can also be performed with small amounts of Ir, Rh, Ru, Pb, Cd, Hg, Tl, Pd, Pt, or Au. One of these chemical sensitization methods or a combination thereof can be used.

The light-sensitive silver halide emulsions can be spectrally sensitized with methine dyes such as those described by F. M. Hamer in "The Cyanine Dyes and Related Compounds", 1964, John Wiley & Sons. Dyes that can be used for the purpose of spectral sensitization include cyanine dyes, merocyanine dyes, complex cyanine dyes, complex merocyanine dyes, homopolar cyanine dyes, hemicyanine dyes, styryl dyes and hemioxonol dyes. Particularly valuable dyes are those belonging to the cyanine dyes, merocyanine dyes, complex merocyanine dyes.

Other dyes, which per se do not have any spectral sensitization activity, or certain other compounds, which do not substantially absorb visible radiation, can have a supersensitization effect when they are incorporated together with said spectral sensitizing agents into the emulsion. Suitable supersensitizers are i.a. heterocyclic mercapto compounds containing at least one electronegative substituent as described e.g. in U.S. Pat. No. 3,457,078, nitrogen-containing heterocyclic ring-substituted aminostilbene compounds as described e.g. in U.S. Pat. No. 2,933,390 and U.S. Pat. No. 3,635,721, aromatic organic acid/formaldehyde condensation products as described e.g. in U.S. Pat. No. 3,743,510, cadmium salts, and azaindene compounds.

The binders of the photographic element, especially when the binder used is gelatin, can be hardened with appropriate hardening agents such as those of the epoxide type, those of the ethylenimine type, those of the vinylsulfone type e.g. 1,3-vinylsulphonyl-2-propanol, chromium salts e.g. chromium acetate and chromium alum, aldehydes e.g. formaldehyde, glyoxal, and glutaraldehyde, N-methylol compounds e.g. dimethylolurea and methyloldimethylhydantoin. dioxan derivatives e.g. 2,3-dihydroxy-dioxan, active vinyl compounds e.g. 1,3,5-triacryloyl-hexahydro-s-triazine, active halogen compounds e.g. 2,4-dichloro-6-hydroxy-s-triazine, and mucohalogenic acids e.g. mucochloric acid and mucophenoxychloric acid. These hardeners can be used alone or in combination. The binders can also be hardened with fast-reacting hardeners such as carbamoyl-pyridinium salts of the type described in U.S. Pat. No. 4,063,952.

The photographic element of the present invention may further comprise various kinds of surface-active agents in the photographic emulsion layer or in at least one other hydrophilic colloid layer. Suitable surface-active agents include non-ionic agents such as saponins, alkylene oxides e.g. polyethylene glycol, polyethylene glycol/polypropylene glycol condensation products, polyethylene glycol alkyl ethers or polyethylene glycol alkylaryl ethers, polyethylene glycol esters, polyethylene glycol sorbitan esters, polyalkylene glycol alkylamines or alkylamides, silicone-polyethylene oxide adducts, glycidol derivatives, fatty acid esters of polyhydric alcohols and alkyl esters of saccharides; anionic agents comprising an acid group such as a carboxy, sulpho, phospho, sulphuric or phosphoric ester group; ampholytic agents such as aminoacids, aminoalkyl sulphonic acids, aminoalkyl sulphates or phosphates, alkyl betaines, and amine-N-oxides; and cationic agents such as alkylamine salts, aliphatic, aromatic, or heterocyclic quaternary ammonium salts, aliphatic or heterocyclic ring-containing phosphonium or sulphonium salts. A preferred class consists of compounds bearing perfluorinated alkyl groups. The surface-active agents can be used for various purposes e.g. as coating aids, as compounds preventing electric charges, as compounds improving slidability, as compounds facilitating dispersive emulsification, as compounds preventing or reducing adhesion, and as compounds improving the photographic characteristics e.g. higher contrast, sensitization, and development acceleration.

Development acceleration can be accomplished with the aid of various compounds, preferably polyalkylene derivatives having a molecular weight of at least 400 such as those described in e.g. U.S. Pat. Nos. 3,038,805–4,038,075–4,292,400.

The photographic element of the present invention may further comprise various other additives such as e.g. compounds improving the dimensional stability of the photographic element, UV-absorbers, spacing agents and plasticizers.

Suitable additives for improving the dimensional stability of the photographic element are i.a. dispersions of a water-soluble or hardly soluble synthetic polymer e.g. polymers of alkyl (meth)acrylates, alkoxy(meth)acrylates, glycidyl (meth)acrylates, (meth)acrylamides, vinyl esters, acrylonitriles, olefins, and styrenes, or copolymers of the above with acrylic acids, methacrylic acids, Alpha-Beta-unsaturated dicarboxylic acids, hydroxyalkyl (meth)acrylates, sulphoalkyl (meth)acrylates, and styrene sulphonic acids.

In general, the average particle size of spacing agents is comprised between 0.2 and 10 um. Spacing agents can be soluble or insoluble in alkali. Alkali-insoluble spacing agents usually remain permanently in the photographic element, whereas alkali-soluble spacing agents usually are removed therefrom in an alkaline processing bath. Suitable spacing agents can be made i.a. of polymethyl methacrylate, of copolymers of acrylic acid and methyl methacrylate, and of hydroxypropylmethyl cellulose hexahydrophthalate. Other suitable spacing agents have been described in U.S. Pat. No. 4,614,708.

The photographic silver halide emulsions can be used in various types of photographic elements such as i.a. in photographic elements for graphic arts and for so-called amateur and professional photography, diffusion transfer reversal photographic elements, low-speed and high-speed photographic elements.

In a preferred embodiment the stabilizers according to the present invention are incorporated in diffusion transfer reversal material, preferably in the emulsion layer of a DTR mono-sheet element. In this type of material the emulsion is usually a chloride rich emulsion. Beside the emulsion layer and the image receiving layer other hydrophilic layers are usually present, e.g. an intermediate layer and a backing layer.

In the image receiving layer, preferred development nuclei are sulphides of heavy metals e.g. sulphides of antimony, bismuth, cadmium, cobalt, lead, nickel, palladium, platinum, silver, and zinc. Especially suitable development nuclei are palladium sulphide nuclei. Other suitable development nuclei are salts such as e.g. selenides, polyselenides, polysulphides, mercaptans, and tin(II) halides. Heavy metals, preferably silver, gold, platinum, palladium, and mercury can be used in colloidal form.

The intermediate hydrophilic layer, serving as antihalation layer, is provided between the support and the silver halide emulsion layer. This layer can contain light-absorbing dyes as described in i.a. U.S. Pat. No. 4,092,168, U.S. Pat. No. 4,311,787, DE 2,453,217, and GB 7,907,440; as alternative finely divided carbon black can be used for the same antihalation purposes as described in U.S. Pat. No. 2,327,828. Further this layer can contain hardening agents, matting agents, e.g. silica particles, and wetting agents.

In a preferred embodiment a backing layer is provided at the non-light sensitive side of the support. This layer which can serve as anti-curl layer can contain i.a. matting agents e.g. silica particles, lubricants, antistatic agents, light absorbing dyes, opacifying agents, e.g. titanium oxide and the usual ingredients like hardeners and wetting agents.

The silver halide developing agent used in the DTR mono-sheet element or/and the developing solution according to the present invention is preferably a p-dihydroxybenzene compound, e.g. hydroquinone, methylhydroquinone or chlorohydroquinone, preferably in combination with an auxiliary developing agent being a 1-phenyl-3-pyrazolidinone-type developing agent and/or p-monomethylaminophenol. Particularly useful auxiliary developing agents are 1-phenyl-3-pyrazolidinone, 1-phenyl-4-monomethyl-3-pyrazolidinone, and 1-phenyl-4,4-dimethyl-3-pyrazolidinone.

Preferred silver halide solvents in the DTR process are watersoluble thiosulphate compounds such as ammonium and sodium thiosulphate, or ammonium and alkali metal thiocyanates. Other useful silver halide solvents (or "complexing agents") are described in the book "The Theory of the Photographic Process" edited by T. H. James, 4th edition, p. 474–475 (1977), in particular sulphites and uracil. Further interesting silver halide complexing agents are cyclic imides, preferably combined with alkanolamines, as described in U.S. Pat. No. 4,297,430 and U.S. Pat. No. 4,355,090. 2-mercaptobenzoic acid derivatives are described as silver halide solvents in U.S. Pat. No. 4,297,429, preferably combined with alkanolamines or with cyclic imides and alkanolamines.

According to a well known conventional embodiment the silver halide emulsion contained in the DTR element is orthochromatically sensitized with a conventional cyanine or merocyanine dye so that said DTR element can be exposed on a process camera using an ordinary light source, e.g. tungsten light. According to more recent developments new types of DTR elements are used as recording materials for phototype-setting and image-setting devices which employ laser beams, e.g. a HeNe laser or a laserdiode, as their output energy source. According to these so-called "direct to plate" methodes these laser-exposed DTR materials are transformed in direct-to-use printing plates containing type- and image information, thus avoiding the intermediate steps as in conventional pre-press work flow. As a consequence these DTR elements must show a spectral sensitivity matching as closely as possible the emission wavelength of the laser beam in question.

The development and diffusion transfer can be initiated in different ways e.g. by rubbing with a roller that has been wetted with the processing liquid, e.g. acts as meniscus coater, by wiping with an absorbent means e.g. with a plug of cotton or sponge, or by dipping the material to be treated in the liquid composition. Preferably, they proceed in an automatically operated apparatus such as RAPILINE SP 430, or a camera processor such as SP 400, marketed by AGFA. The DTR-process is normally carried out at a temperature in the range of 10° C. to 35° C. In order to minimize the quality loss due to bath exhaustion, regenerating liquids can be added in proportion to the consumption of processing liquids.

The following examples illustrate the present invention without however, limiting it thereby. All parts, percentages and ratios are by weight unless otherwise indicated.

EXAMPLE 1

Preparation of Compound I-2

This preparation occurs through following chemical reaction steps:

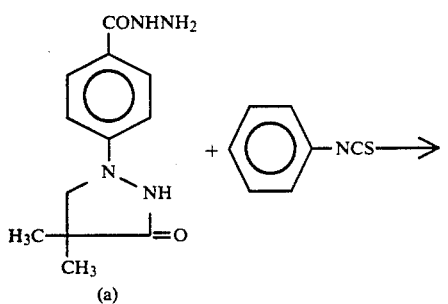

(a)

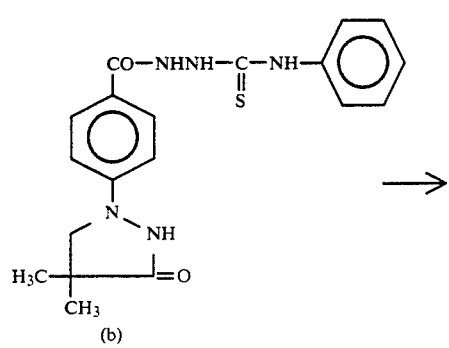

(b)

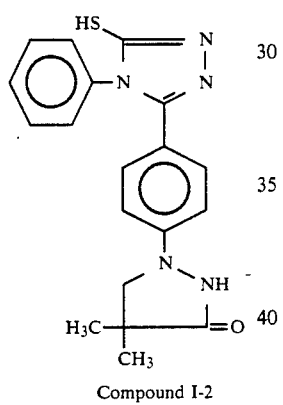

Compound I-2

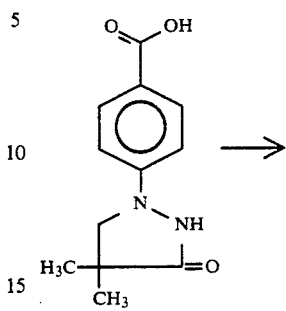

(1)

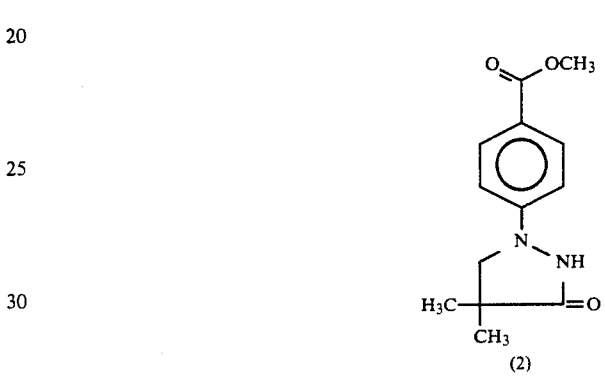

(2)

(3)

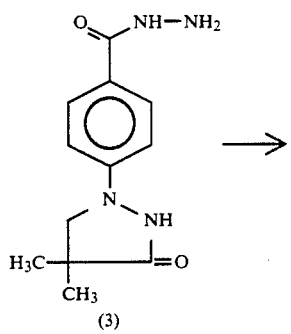

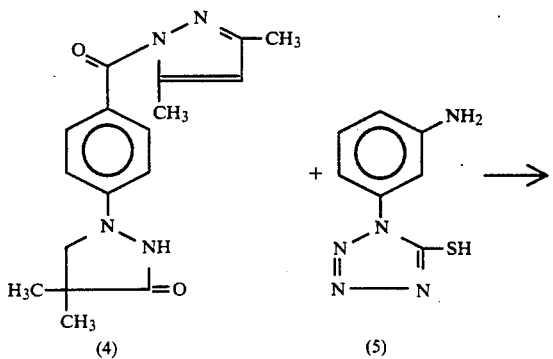

(4)  (5)

To a suspension of 24.8 g (0.1 mole) of compound (a) in 200 ml anhydrous ethanol, a solution of 15.5 g (0.115 mole) phenylisothiocyanate in 100 ml anhydrous ethanol is added whilst stirring. After 30 minutes of boiling a voluminous precipitate is formed. This precipitate (intermediate (b)) is filtered off and washed with 300 ml warm ethanol. Yield: 38.5 g (100%); melting point: 210° C.

A suspension of 38.3 g (0.1 mole) of compound (b) in 1000 ml 2N NaOH is boiled under reflux until a solution is formed. The cooled reaction mixture is poured into a mixture of 450 ml 5N HCl and 250 g ice-water. The precipitate is stirred for 30 minutes, filtered off, washed with water and recrystallized from ethanol. Yield: 24.8 g (67%); melting point: >260° C.

EXAMPLE 2

Preparation of Compound I-3.

The preparation of Compound I-3 proceeds through following intermediate products (1) to (5):

-continued

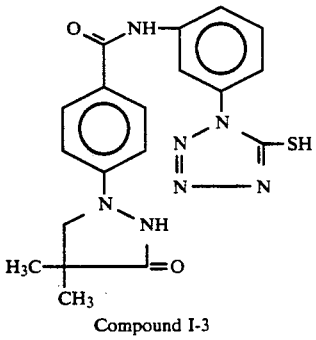

Compound I-3

Preparation of Intermediate (1)

The preparation proceeds according to the one described in EP 0196705 (see p. 5, "preparation of developing agent 2").

Preparation of Intermediate (2)

To a suspension of 46.8 g (0.2 mole) of (1) in 100 ml methanol was added 26.1 ml of thionylchloride (0.22 mole). The temperature rose to 50° C. The reaction mixture was kept boiling for 7 hours. After cooling the formed precipitate was separated by filtration and washed with methanol.

Yield: 34.2 g; melting point: 162° C.

Preparation of Intermediate (3)

A suspension of 124 g (0.5 mole) of (2) in 194 ml (4 mole) hydrazinehydraat was heated at 50° C. for 3 hours. After cooling the reaction mixture was poured in 800 ml ice-water. The formed precipitate was filtered and washed with water.

Yield: 84.4 g; melting point: 254° C.

Preparation of Intermediate (4)

To a suspension of 426 g (2 mole) of (3) in 2.5 l of ethanol and 280 ml of 5N HCl was added 250 g (2.5 mole) 2,4-pentanedione dissolved in 250 ml of ethanol. The reaction mixture is stirred at 5° C. for 1 hour. The formed precipitate was washed with water and ethanol and dried.

Yield: 532 g; melting point: 167° C.

Preparation of Compound I-3

To a solution of 144.75 g (0.75 mole) of 1-(3-aminophenyl)-5-mercapto-tetrazole (5) in 3.75 l acetic acid was added 234 g (0.75 mole) of (4). The reaction mixture was stirred at 60° C. for 6 hours. After cooling the reaction mixture was poured in 3.75 l water. The formed precipitate was filtered, washed with water and dried.

Yield: 229.9 g; melting point: 250° C.

EXAMPLE 3

A photographic DTR mono-sheet material was prepared as follows. One side of a transparent polyethyleneterephtalaat film, covered on both sides with a subbing layer was coated with two layers by a double layer coating technique. The layer nearest to the support constituted the antihalation layer, the other one was the emulsion layer. The emulsion was a typical chlorobromide emulsion composed of 98.2% of chloride and 1.8% of bromide, having a mean grain size of 0.3 micron and containing Rhodium ions as an internal dopant. This emulsion was sensitized for wavelenghts longer than 700 nm and stabilized with Compound R-1. The emulsion layer contained 1.5 g of silver halide expressed as $AgNO_3$, 0.1 g of 1-phenyl-3-pyrazolidinone and 1.0 g of gelatin per sqm. The antihalation layer contained carbon black, silica particles of 5 micron average size and gelatin at 3 $g/m^2$. The gelatin was lime treated, substantially free of calcium ions (1000 ppm or less).

After drying these layers were subjected to a temperature of 40° C. for 5 days and then overcoated with a layer containing Pds nuclei, hydrochinon at 0.4 $g/m^2$ and formaldehyde at 100 $mg/m^2$.

The following processing solutions were prepared:

| Activator solution | | |
|---|---|---|
| sodium hydroxide | 25 | g |
| sodium sulphite anh. | 40 | g |
| potassium thiocyanate | 20 | g |
| 3-mercapto-4-acetamido-5-n.heptyl-1,2,4-triazole | 0.5 | g |
| water to make | 1 | l |
| Neutralization solution | | |
| citric acid | 10 | g |
| sodium citrate | 35 | g |
| cysteine | 1 | g |
| sodium sulphite anh. | 5 | g |
| phenol | 50 | mg |
| water to make | 1 | l |
| Dampening solution | | |
| water | 880 | ml |
| citric acid | 6 | g |
| boric acid | 8.4 | g |
| sodium sulphate anh. | 25 | g |
| ethyleneglycol | 100 | g |
| colloidal silica | 28 | g |

The above described DTR material was image-wise exposed in the image-setter CG 9400, containing a laserdiode, marketed by AGFA COMPUGRAPHIC, a division of AGFA CORPORATION; subsequently the material was treated with the described activator solution for 10 seconds at 30° C., thereupon treated with the described neutralization solution at 25° C. and finally dried.

The printing plate thus prepared was mounted on an offset printing machine (AB DICK 350 CD-trade name for offset printing machine manufactured by AB DICK Co). During the printing run the described dampening solution was used in each case.

The sensitometric properties of this material were characterized by the minimal and maximal density, the gradation measured between 25% and 75% of the maximal density, and the sensitivity (S) expressed as relative log Et value determined at density 1.0. A lower value number for S stands for higher sensitivity and vice versa. A decrease of the value by 0.30 means a doubling of the sensitivity.

The lithographic properties printing endurance and background stain were evaluated as follows:

a) printing endurance: number of printed copies before disappearance of ink in the ink accepting areas begins to occur:

X: 2000–5000

O: more than 5000 b) background stain: the feeding of paper was started as soon as the inking roll was brought into contact with the surface of the printing plate; copies obtained after 1000 impressions were evaluated as follows:

O: no stain
\#: partial stain or slight stain over the non-image areas
X: heavy stain all over the non-image areas.

Other DTR materials were composed according to example 3 but instead of Compound R-1, Compounds I-1 and I-3 were used as stabilizers at a concentration of $5.10^{-3}$ mole per mole $AgNO_3$.

The results are summarized in table 1:

TABLE 1

| stabilizer | Dmin | Dmax | grad | S | stain | endurance |
|---|---|---|---|---|---|---|
| Comp R-1 | 0.56 | <1.00 | — | — | — | — |
| I-1 | 0.62 | 1.24 | 0.57 | 2.16 | 0 | 0 |
| I-3 | 0.56 | 1.24 | 0.73 | 2.08 | 0 | 0 |

The table illustrates the speed- and gradation increase on using the compounds of the invention. With comp. R-1 no sensible values can be given.

EXAMPLES 6-7

In example 6 a DTR material analogous to example 3 was prepared but the emulsion was red sensitized instead of infra-red and stabilized with the known naphtoxathiazol Compound R-2 as reference. Example 7 was stabilized with compound I-3 according to the invention. The DTR materials were image-wise exposed in the image-setter CG 9600, marketed by AGFA COMPUGRAPHIC, a division of AGFA CORPORATION; this image-setter contains a HeNe laser as exposure source. These materials were subsequently treated with the described activator and neutralization solutions and finally dried.

The results of examples 6 and 7 are summarized in table 2.

TABLE 2

| stabilizer | Dmin | Dmax | Grad. | S[1] | stain | endurance |
|---|---|---|---|---|---|---|
| R-2 | 0.56 | 1.24 | 1.00 | 100 (ref.) | 0 | X |
| I-3 | 0.54 | 1.25 | 1.15 | 85 | 0 | 0 | note 1: lower value number means higher sensitivity expressed in relative log Et values.

Table 2 again shows the beneficial effect of a compound according to the invention on the sensitometric characteristics and also illustrates the better lithographic performance.

EXAMPLES 8-9

In example 8 a typical graphic arts emulsion consisting of 83,6% chloride, 16% bromide and 0.4% iodide, and containing Rhodium and Iridium dopants was prepared. The mean grain size was 0.30 micron. The emulsion was chemically sensitized with sulfur and gold compounds and stabilized with Compound R-1. The emulsion was coated at 7 g $AgNO_3/m^2$ on polyethyleneterephtalate film and served as a reference.

Example 9 was identical to the previous one with the exception that the emulsion was stabilized with Compound I-4.

The above described graphic arts material was image-wise exposed in the image-setter CG 9400, marketed by AGFA COMPUGRAPHIC, a division of AGFA CORPORATION; this image-setter contains a laserdiode as exposure source. The material was subsequently developed in a classical negative working hydrochinon-phenidone developer and fixed in a classical thiosulphate containing fixing solution. Measured on a DAI-NIPPON SCREEN densitometer the comparative example 8 shows practically no formation of density while example 9 according to the invention shows a speed increase compared to example 8 of at least 1.00 log Et.

We claim:

1. Photographic material comprising a support and at least one light-sensitive silver halide emulsion layer characterized in that said material contains in said emulsion layer or in a hydrophylic layer in water-permeable relationship therewith at least one 1-phenyl-3-pyrazolidinone derivative according to the general formula:

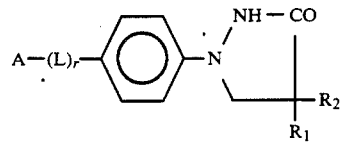

wherein:
A represents a group capable of adsorbing at the surface of silver halides;
L is a divalent linking group and r is 0 or 1;
$R_1$ and $R_2$ each represent hydrogen, lower alkyl or substituted lower alkyl.

2. Photographic material according to claim 1 wherein the group A is a moiety chosen from the list of thiourea, triazoles, mercaptotetrazoles, mercaptoimidazoles, mercaptothiazoles, mercaptooxazoles, mercaptotriazoles, indazoles, imidazoles, benzimidazoles, 7-hydroxy-s-triazolo-[1,5-a]-pyrimidines.

3. Photographic material according to claim 1 wherein the photographic material is a diffusion transfer reversal (DTR) material.

4. Photographic material according to claim 3 wherein the said DTR material is a DTR mono-sheet element capable of being transformed by processing into a planographic printing plate.

* * * * *